(12) United States Patent
Kinsella, Jr. et al.

(10) Patent No.: US 11,241,538 B2
(45) Date of Patent: Feb. 8, 2022

(54) DEVICE AND METHOD FOR IMPROVING RETENTION OF A THERAPY IN THE BLADDER

(71) Applicant: Watershed Medical, Inc., Believe, WA (US)

(72) Inventors: Christopher Ralph Kinsella, Jr., Los Altos, CA (US); Clay Nolan, Morgan Hill, CA (US); Rush Bartlett, Austin, TX (US)

(73) Assignee: Watershed Medical, Inc., Bellevue, WA (US)

( * ) Notice: Subject to any disclaimer, the term of this patent is extended or adjusted under 35 U.S.C. 154(b) by 9 days.

(21) Appl. No.: 17/200,313

(22) Filed: Mar. 12, 2021

(65) Prior Publication Data

US 2021/0196888 A1    Jul. 1, 2021

Related U.S. Application Data

(63) Continuation of application No. 17/062,469, filed on Oct. 2, 2020, now abandoned.

(60) Provisional application No. 62/909,237, filed on Oct. 2, 2019, provisional application No. 62/910,104, filed on Oct. 3, 2019, provisional application No. 63/029,296, filed on May 22, 2020.

(51) Int. Cl.
*A61M 5/178*     (2006.01)
*A61K 9/16*      (2006.01)
*A61K 9/00*      (2006.01)
*A61K 9/14*      (2006.01)

(52) U.S. Cl.
CPC .......... *A61M 5/178* (2013.01); *A61K 9/0034* (2013.01); *A61K 9/14* (2013.01); *A61K 9/145* (2013.01); *A61K 9/146* (2013.01); *A61K 9/16* (2013.01); *A61K 9/167* (2013.01); *A61K 9/1629* (2013.01); *A61M 2210/1085* (2013.01); *A61M 2210/1089* (2013.01)

(58) Field of Classification Search
CPC .......... A61M 5/178; A61M 2210/1085; A61M 2210/1089; A61K 9/16; A61K 9/14; A61K 9/0014; A61K 9/146; A61K 9/1629; A61K 9/145; A61K 9/167
See application file for complete search history.

(56) References Cited

U.S. PATENT DOCUMENTS

| | | |
|---|---|---|
| 4,871,542 A | 10/1989 | Vilhardt |
| 6,183,461 B1 | 2/2001 | Matsuura et al. |
| 6,524,608 B2 | 2/2003 | Ottoboni et al. |
| 6,572,532 B1 | 6/2003 | Pratt et al. |
| 9,457,176 B2 | 10/2016 | Lee et al. |

(Continued)

FOREIGN PATENT DOCUMENTS

| | | |
|---|---|---|
| EP | 3069729 | 9/2016 |
| WO | WO 2005/115245 | 12/2005 |

(Continued)

OTHER PUBLICATIONS https://my.clevelandclinic.org/health/diseases/15427-urinary-retention (Year: 2021).*

*Primary Examiner* — Carlos A Azpuru
(74) *Attorney, Agent, or Firm* — Levine Bagade Han LLP

(57) ABSTRACT

Devices that are placed within fluid filled organs, such as the bladder, which reduce the risk of bacterial infections using a combination of active agents and mechanical disruption of bacteria.

15 Claims, 7 Drawing Sheets

(56) References Cited

U.S. PATENT DOCUMENTS

| | | |
|---|---|---|
| 2001/0019719 A1 | 9/2001 | Ottoboni et al. |
| 2004/0260272 A1 | 12/2004 | Friedman et al. |
| 2005/0175709 A1 | 8/2005 | Baty, III et al. |
| 2006/0009587 A1 | 1/2006 | Kim et al. |
| 2008/0119927 A1 | 5/2008 | Lessar |
| 2011/0251574 A1 | 10/2011 | Hedrich et al. |
| 2017/0127929 A1 | 5/2017 | Schutt et al. |
| 2017/0360040 A1 | 12/2017 | Kost et al. |
| 2018/0193618 A1 | 7/2018 | Erbey et al. |
| 2020/0086104 A1 | 3/2020 | Choi et al. |
| 2021/0100950 A1 | 4/2021 | Kinsella et al. |

FOREIGN PATENT DOCUMENTS

| | | |
|---|---|---|
| WO | WO 2019/227092 | 11/2019 |
| WO | 2020/069376 A1 * | 4/2020 |
| WO | WO 2020/069376 | 4/2020 |
| WO | WO 2021/067857 | 4/2021 |

* cited by examiner

DEVICE AND METHOD FOR IMPROVING RETENTION OF A THERAPY IN THE BLADDER

CROSS-REFERENCE TO RELATED APPLICATIONS

This application is a continuation of U.S. patent application Ser. No. 17/062,469 filed on Oct. 2, 2020, which claims the benefit of U.S. Provisional Application No. 62/909,237 filed Oct. 2, 2019, which also claims the benefit of U.S. Provisional Application No. 62/910,104 filed on Oct. 3, 2019 and of U.S. Provisional Application No. 63/029,296 filed May 22, 2020, the entireties of each of which are incorporated by reference.

FIELD OF THE INVENTION

Devices that are placed within fluid filled organs, such as the bladder, which reduce the risk of bacterial infections using a combination of active agents and mechanical disruption of bacteria.

BACKGROUND OF THE INVENTION

Urinary tract infections ("UTI") are infections in any part of the urinary system, such as the kidneys, ureter, bladder, and/or urethra. The UTI typically develops in the human bladder caused by the migration of bacteria into the bladder cavity through the urethra. UTI's are one of the most common types of infections that require medical treatment. Nearly, one in five adults develops a UTI and many of these individuals are at risk for a recurring infection.

The risks associated with UTI's can be significant for persons suffering from incontinence or for older persons, as well as with traumatic changes in the central nervous system, which are accompanied by urination disorders. In many cases, chronic urinary tract infections can require continuous medication, which, leads to progressive levels of resistance to antibiotics and ultimately to kidney problems.

UTI's and complications caused by UTI's are cost-intensive due to continuous need for medication and extended hospitalization and they can be life-threatening. In many cases, UTI's significantly reduce the quality of life, in particular when kidney damage leads to kidney failure requiring dialysis or implantation of a donor kidney.

In many cases, the UTI is only treated after the infection has developed and becomes symptomatic. However, current treatment to prevent the formation of UTI's requires continuous prophylactic oral intake of medication that can potentially strain the entire body, in particular with long-term medication. However, the increase of multi-drug resistant bacteria makes it harder to treat UTI's with a standard anti-biotic regimen as the UTI can recur since all of the bacteria causing the UTI are not eliminated.

The problems arising from bladder infections is that the infection can ascend to the kidney via the ureter. In many cases women are at greater risk of developing a UTI than are men. While the infection can be limited to the bladder and produce pain, serious consequences can occur if a UTI spreads to the kidneys or other organs as sepsis (urosepsis) can occur. The problem is increased in the elderly because UTI's are especially prevalent with incomplete voiding of the bladder, weakened immune systems, dehydration, and adult diapers, where such factors increase the risk of UTI. In many cases elderly patients do not present with typical signs of infection until they become septic, at which point the patient requires hospitalization.

In Systemic delivery of drugs to treat UTIs, the volume of distribution of the therapy is equal to the total amount of urine which enters the bladder. Therefore, the therapy is voided with each emptying of the bladder and requires constant replenishment. In other cases, the drug target can be limited (i.e., the bladder wall) but cannot practically be reached without raising the concentration of the drug in the urine to the desired therapeutic concentration.

For conditions related to urinary tract infection, clearance of the bacteria is improved with complete emptying of the bladder. If the bladder does not empty efficiently, there is a retained volume of urine termed the "post void residual" which can act as a reservoir of bacteria for subsequent and ongoing infection. Detecting and minimizing this post void residual urine volume faces several challenges, namely: post void residual can be measured indirectly through ultrasound assessment, however this has limited accuracy depending on body habitus and at volumes less than 50 ml and greater than 250 ml. The post void residual can be measured and removed by draining the remaining urine through a catheter inserted retrograde through the urethra, however this is painful and can be psychologically traumatizing especially in the case of pediatric individuals.

Post void residual can also be decreased by removing the primary cause of bladder outlet obstruction, such as widening an area of urethral narrowing. However, this approach often requires a separate procedure or surgery.

Removal of the post void residual urine volume without treating the underlying cause for the retained urine is a temporary maneuver as the volume will reaccumulate by the next voiding cycle. Without a procedure or surgery, this volume will remain and can be a potential reservoir of future and ongoing infection.

Therefore, there is a need to prevent and/or reduce the survival of bacteria within the bladder, where such an approach does not cause collateral risk to the patient. Such a treatment can provide benefits for patients at risk of a UTI. Such especially benefits for incapacitated patients or the elderly, where the treatment eliminates the need for long term prophylactic administration of antibiotics and still reduces or eliminates a patient's risk of developing a UTI.

BRIEF SUMMARY OF THE INVENTION

The illustrations and variations described herein are meant to provide examples of the methods and devices of the invention. It is contemplated that combinations of aspects of specific embodiments or combinations of the specific embodiments themselves are within the scope of this disclosure.

The present disclosure includes devices for reducing infections within a fluid filled organ using a combination of anti-bacterial properties and mechanical disruption of biofilms that would otherwise allow bacterial growth. The devices and methods described herein rely on particles for treating and/or preventing urinary tract infections in an individual. These particles are intended to function as implants or particle-implants that are retained by a wall of the bladder or other organ over an extended period of time and/or through multiple cycles of filling and emptying of the bladder.

The present disclosure includes device for delivering a substance into a urinary bladder and/or devices for deploying a temporary implant into the urinary bladder in an individual. In one example such devices include a plurality of particles where at least each particle of the plurality of particles has a buoyancy resulting in flotation of the plurality of particles in a urine contained in a bladder of the individual, where a size of each particle of the plurality of particles is within a pre-determined size range; each particle of the plurality of particles comprising an active substance having an anti-bacterial property; and wherein the plurality of particles are constrained in a delivery unit to permit passage of the plurality of particles through a urethra of the individual and into the bladder.

The particles can include one or more therapeutic substance. Such therapeutic substance can include, but are not limited to a urease inhibitor, a chelating agent, an antibacterial agent, an enzyme, and a combination thereof.

In additional variations, the particles can further include a carrier substance. Such a carrier substance can comprise a degradable material, a non-degradable material, or a combination thereof. In additional variations, the therapeutic substance is located within and/or coated on the carrier substance. Examples of carrier substances include, but are not limited to a polymer, lipid, or a glass material. Moreover, any of the particles and/or carrier substances can be porous or non-porous.

Additional variations of the devices can include a plurality of secondary particles each having therapeutic properties where at least each secondary particle of the plurality of secondary particles has a buoyancy resulting in sinking of the plurality of particles in the urine contained in the bladder of the individual.

The density of particles in the present device can be less than 1 kg/m^3. An example of a size of the particle can include a pre-determined size range of less than 400 micrometers.

Variations of the device can include a delivery form that is a syringe or a sealed container.

The present disclosure also includes methods for treating and/or preventing urinary tract infections in an individual. For example such methods can include providing a plurality of particles each having therapeutic properties where at least each particle of the plurality of particles has a buoyancy resulting in flotation of the plurality of particles in a urine contained in a bladder of the individual, where a size of each particle of the plurality of particles falls within a pre-determined size range; and delivering the plurality of particles through a urethra of the individual into the bladder wherein the plurality of particles float to a surface of the urine, such that upon contraction of the bladder one or more rugae on a wall of the bladder contracts to form a fold in tissue, where a combination of the buoyancy and the pre-determined size range of the plurality of particles causes the one or more rugae to encase the plurality of particles in the fold of tissue such that a number of particles is retained in the bladder over a series of cycles in which the bladder refills and empties with urine.

The methods described herein can also include delivery of the plurality of particles through a urethra of the individual into the bladder to produce a mechanical disruption of a biofilm. Such mechanical disruption can occur anywhere in the fluid path of the particle such as the urethra, bladder, and/or a catheter in fluid contact with either the urethra and/or bladder.

The present disclosure can also include a method of delivering groups of differently sized particles and determining which size is best retained for treatment of an individual patient.

The present disclosure describes devices and methods for the intravesicular delivery of therapeutically active agents or materials to the bladder, urinary tract, ureters, urethera, or other privileged mammalian sites for local or systemic use. The therapy includes but is not limited to the delivery of therapeutically active substances to the human organs such as the bladder to provide local or systemic therapeutic effects. These effects may include but should not be limited to the prevention, treatment, or diagnosis of urinary tract infection, pathogen identification as to the presence of specific pathogens or colonization of the urinary tract or bladder, stimulation of the bladder to more fully expel material, reduction of inflammation, stimulation of inflammation, or other methods to otherwise modify, effect, or treat a condition of the bladder and urinary tract system.

The present methods and device can also be used to decrease the total systemic drug dose requirement for treating an infection of a contracting organ with a central lumen or cavity. In this way pathogenic cell walls and membranes could be compromised through ionic, pH, or osmotic gradient effects to weaken the pathogens or retard their growth such that other therapeutic doses of drugs or molecular active substances could be used in combination with the present invention to provide a desired therapeutic benefit for a patient.

The present disclosure also relates to devices for intravesicular drug delivery as a method for minimization or stimulation of the sensory nerves of the bladder trigone in order to provide therapeutic remedy for overactive bladder, modification of the pro-inflammatory neural cascade, or other affliction of the bladder.

The present disclosure also includes variations related to a retention of a therapy within a bladder organ such that these devices could be designed to be indwelling, at least partially, within the bladder in order to maintain a controlled release therapeutic effect over a period of time while they are indwelling in whole or in part during use. This may include devices that are retained within the bladder that degrade or adjust in configuration over time such that portions of the devices are excreted in the urine over time. Other methods of the invention may be used to extend the duration of therapy for a device within a bladder organ such as the inclusion of coatings or surface configurations which would enable the device to be retained with minimal inflammation and or complications to the bladder.

The particle-implants described herein can also improve reducing or eliminating post void residual volume from the bladder since the particles can displace urine during the voiding or contraction process.

The particle-implants described herein do not require removal using specialized tools. Moreover, the increased retention of particles solely residing in the bladder allow for increased therapeutic dosage levels that would be discouraged if administered systemically.

The present disclosure also includes particle-implants consisting of a plurality of buoyant bodies with a therapeutic agent (e.g., anti-biotic). The therapeutic agent may be present as a coating, as part or whole of the structure of the buoyant body or be contained within a cavity of the buoyant body. The coating or structure of the buoyant body may differ in thickness, composition, or structure within a single body or across the plurality of bodies so as to create a uniform or non-uniform rate of release for the therapeutic agent or a uniform or non-uniform rate of degradation of the buoyant body. The coating may degrade or not degrade as is preferred for the performance of the release profile and concentration gradient within the retained and accumulating volume of urine within the bladder. Materials that could be used to construct the buoyant bodies may include but not be limited to any of the following such as, polycaprolactone, chitosan, polyethylene glycol, poly lactic acid, poly lactic-co-glycolic acid, n'n-isopropylacrylamide, acrylamido taurate, polyethylene, polypropylene, cross linked collagen or gelatin gels, polyacrylamide gels, or glass. Therapeutic agents may comprise one or more but not be limited to, antibiotics, silver, silver ions, colloidal silver, silver nitrate, silver sulfadiazine, ascorybyl palmitate, ascorbic acid, anesthetic agents, lidocaine, bupivacaine, benzocaine, chemotherapy agents, Cisplatin, gemcitabine, methotrexate, monoclonal antibodies, cell therapeutics such as modified or unmodified CAR-T, enzymes, mRNA with or without liposomal delivery vehicles, Loop diuretics such as furosemide (Lasix), Thiazide diuretics such as hydrochlorothiazide, antifibrinolytic compounds, anticoagulant compounds, coagulant compounds, contrast agents such as gadolinium, air bubbles, iodinated contrast, barium sulfate, aluminum or aluminum oxide, iron or iron oxide, gold or gold compounds, pH or precipitate modifying compounds such as hydrochloric acid, EDTA (Ethylenediaminetetraacetic acid), sodium hydroxide, and many others, micro- or nano-encapsulated agents, and or any other combination or sole compound or structure that would enable a therapeutic effect on the desired area through application from a buoyant body delivery vehicle. It should also be noted that the therapeutic elements themselves may be the buoyant body if they are agents that would otherwise at least be partially retained due to their structure, shape, or other features such as if the ionic gradient would enable the material to want to more readily stick to the wall of the bladder or if larger beads of structures such as silver beads with air encapsulated within would result in the therapeutic agent itself in being partially or fully retained until degraded or used. Therapeutic actions may include treatment, prevention, or diagnostic of many conditions or diseases including but not limited to urinary tract infections, bladder cancer, kidney cancer, ureter cancer, urethra cancer, anti-coagulant disease, diagnostic imaging, overactive bladder, underactive bladder, retained urine, diabetes, heart failure (fluid retention and or reduction), kidney failure and or supplementary treatments with dialysis, cystitis, and many other conditions.

Wherein the buoyant bodies could comprise many different configurations with a retained free void volume. These configurations could be spheres, cubes, three-dimensional star shapes or hexagonal shapes, and or any other three-dimensional shape. These buoyant bodies could be hollow, contain a gas, contain a vacuum, contain a liquid, and or contain any other polymer or material such as PLLA, PGLA, PEG, glass, plastic, wood, ceramic, metal, foams, micelles, lipids, hydrophobic materials, hydrophilic materials, polyesters, and or other material such that the density or shape of the buoyant body would enable it to be at least partially retained for therapeutic effect over time. Properties of the materials that comprise the buoyant bodies may be but should not be limited to materials that are hydrophilic or hydrophobic, polar, non-polar, multi-polar, both hydrophobic and hydrophilic depending on pH and or temperature reactive such as with n'n-isopropyl acrylamide, and or other material properties such as electrically conductive or ionizable in solution as a salt. The material should be rapidly and effectively drained through a catheter and or introduced into the bladder through the same effective delivery vehicle or catheter as well as could be instilled with a injection through a catheter or through the tissue itself such that a plug of material, colloid, solution, or other configuration would be delivered into the desired volume in the bladder The devices described herein are suitable for treatment of existing infections as well as for long term prophylactic administration to prevent occurrences of infection. However, unlike conventional prophylactic treatments, the current device does not present the drawbacks of current prophylactic anti-biotic treatments. Moreover, the implants disclosed herein can be intended for temporary, long term, or even permanent placement within the body.

DESCRIPTION OF THE DRAWINGS

Each of the following figures diagrammatically illustrates aspects of the invention. Variation of the invention from the aspects shown in the figures is contemplated.

DETAILED DESCRIPTION

It is understood that the examples below discuss uses of an implant device for either treating a bladder for an existing infection in the urinary tract or for prophylactic administration to prevent an infection from occurring. However, unless specifically noted, variations of the device and method are not limited to use only in the bladder, instead, the device can be used for general surgical procedures to prevent infections from developing in fluid filled organs. For purposes of this disclosure, the term fluid-filled organ can be substituted for bladder. Therefore, the methods and device will have applicability in various parts of the body under any minimally invasive or invasive procedure. Moreover, the invention may be used in any procedure where the benefits of the method and/or device are desired. Furthermore, because it is impractical to display each and every combination of features and aspects of various embodiments, it is understood that where possible, every aspect or feature of an embodiment of the methods and/or devices can be combined with alternate embodiments of methods and/or devices.

Figure 1A:
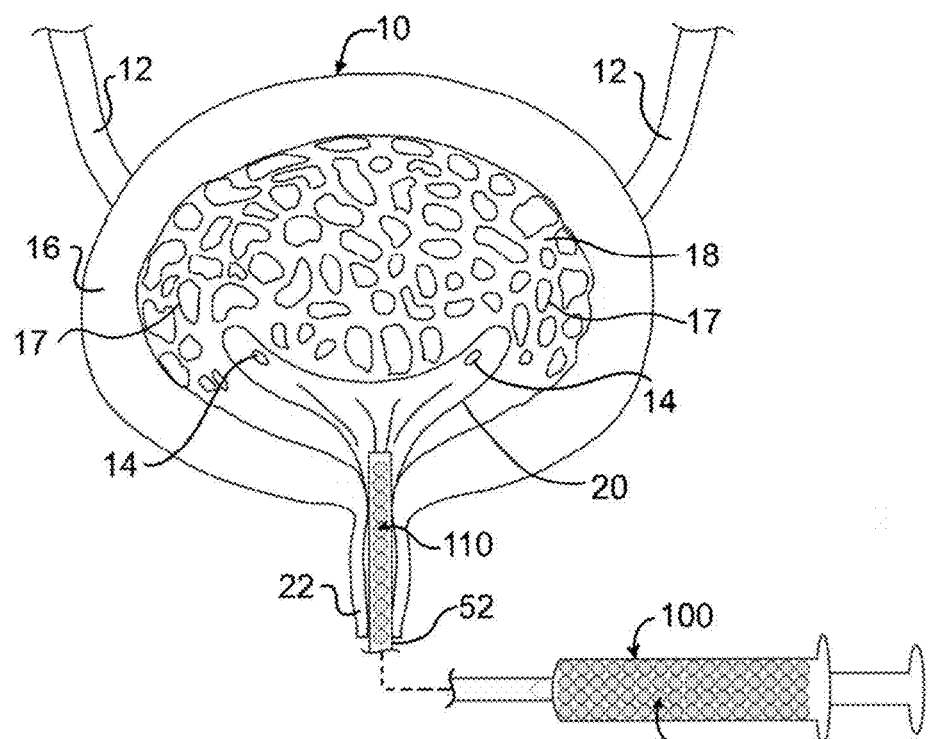
FIGS. 1A and 1B show cross sectional illustrations of a bladder showing the ureters terminating in ureteric orifices within a cavity of the bladder.
Figure 1B:
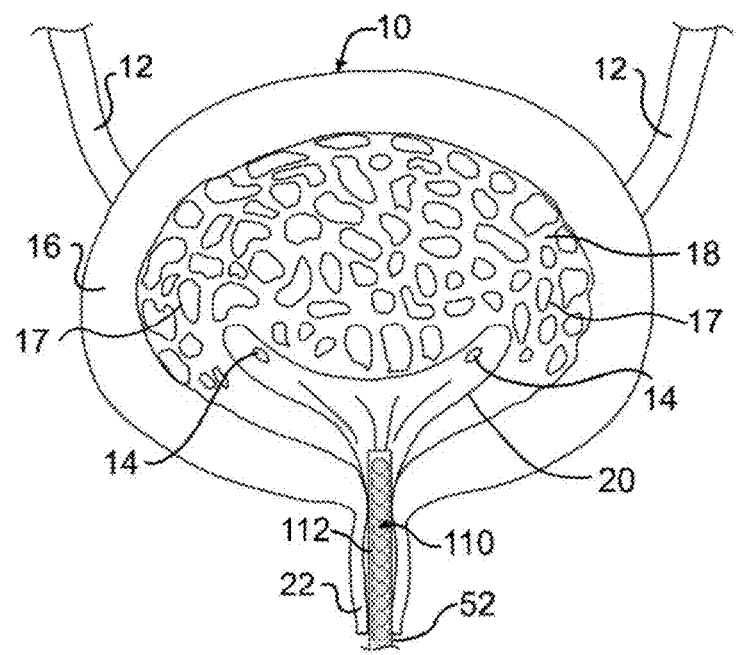

FIGS. 1A and 1B illustrate cross sectional views of a bladder 10 showing the ureters 12 terminating in ureteric orifices 14 within a cavity 18 of the bladder 10. The bladder is surrounded by a muscle in a wall 16 of the bladder. In the illustrated variation, even though the bladder 10 is depicted in an expanded state, it is shown without the presence of any fluid for purposes of illustration. However, as discussed below, fluid can be present in the cavity 18 of the bladder 10 to assist in delivery of therapeutic particles 110 as discussed herein.

The inner lining of the bladder 10 is a mucous membrane of transitional epithelium that contains rugae, which are a series of ridges produced when the walls of the bladder fold during voiding or contraction of the bladder. Likewise, the rugae 17 separate when the bladder expands. When the bladder is full/expanded with urine, the muscle wall of the bladder causes contraction of the bladder causing the bladder to assume a pyramid shape. In this configuration, the rugae collapse into folds.

FIG. 1A illustrates a catheter, tube, or other introducer device 52 that is advanced into the urethra 22, where the delivery device 52 contains a plurality of particles 110 that are delivered from a delivery unit 100. In practice, the delivery unit 100 allows a caregiver to determine the volume of particles 110 delivered into the bladder 10. The volume of particles 110 can vary depending upon the patient being treated. For example, some individuals may require or tolerate a smaller volume of particles 110. Moreover, a caregiver can track the volume of particles delivered into a patient's bladder to monitor an effectiveness of the volume of particles delivered. In some variations, the delivery unit 100 can comprise a set dosage or volume of particles 110 to produce a standard volume of particles that are intended to be delivered. In addition, delivery of individual particles as a space occupying implant provides a volume that is necessary to determine the full amount of post void residual (PVR) for each patient FIG. 1B illustrates a variation similar to that shown in FIG. 1A. However, in FIG. 1A, the particles 110 are separately contained in a delivery unit for deposit directly into the bladder 10. In contrast, as shown in FIG. 1B, the delivery unit can comprise a capsule or other coating 112 restrains a number of particles 110 together. In most variations, the capsule/coating 112 dissolves to release the particles 110. Alternatively, the capsule/coating 112 can be fluid permeable to allow the particles 110 to deliver a therapeutic effect to the bladder. The capsule 112 will dissolve or degrade after a period of time to enable retention of the particles 110 as discussed below. In additional variations, the particles 110 can be deployed in a joined or conglomerate form where each particle 110 is joined to at least another particle 110, where this joined or conglomerate form ultimately breaks down such that individual particles 110 are located within the bladder. In such a case, the delivery unit 112 can comprise the substance that temporarily joins the particles 110.

In both FIGS. 1A and 1B a delivery device 52 advances into the trigone 20 of the bladder 10 so that the particles 110 can be deposited into the cavity 18 of the bladder 10. However, alternate variations are within the scope of this disclosure. For example, delivery of the particles 110 can occur without the use of a delivery device advanced into the urethra. For example, a fluid containing the particles 110 can be flushed into the bladder 10. However, as discussed herein, delivery of the particles 110 through a urethra and directly into the bladder allows for deployment of a higher dosage/concentration of a therapeutic substance into the bladder than would otherwise be possible with a systemic delivery of the same substance.

Alternative variations of the methods described herein can include delivery of particles 110 into the bladder 10 surgically or through an endoscopic approach.

Figure 2A:
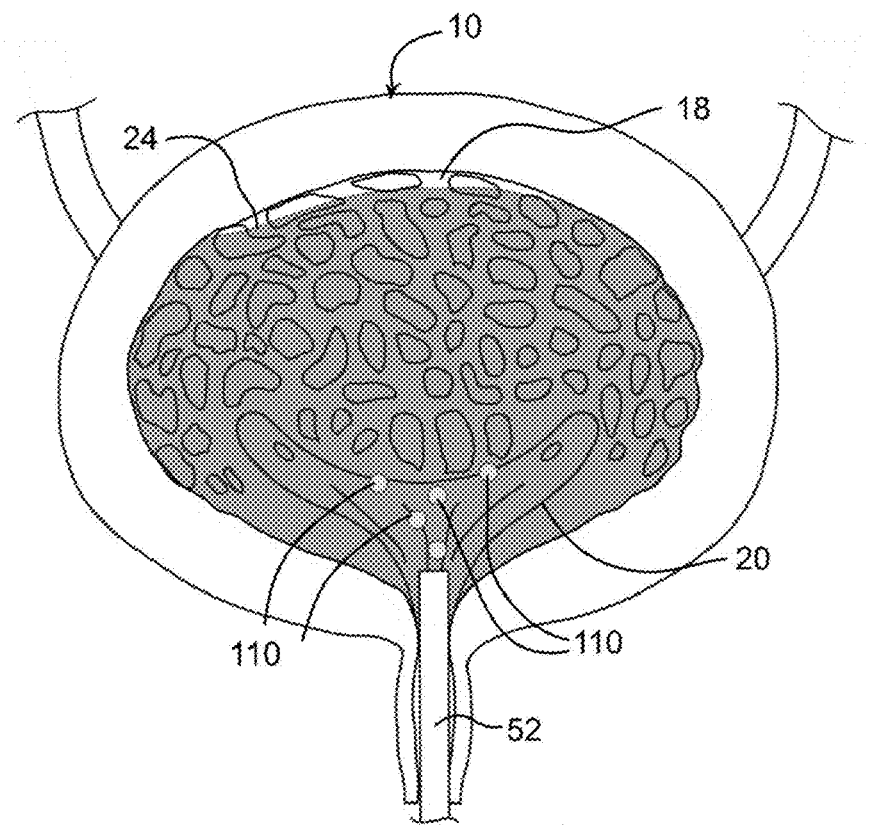
FIGS. 2A and 2B illustrates delivery of particles directly into the bladder through a urethra.
Figure 2B:
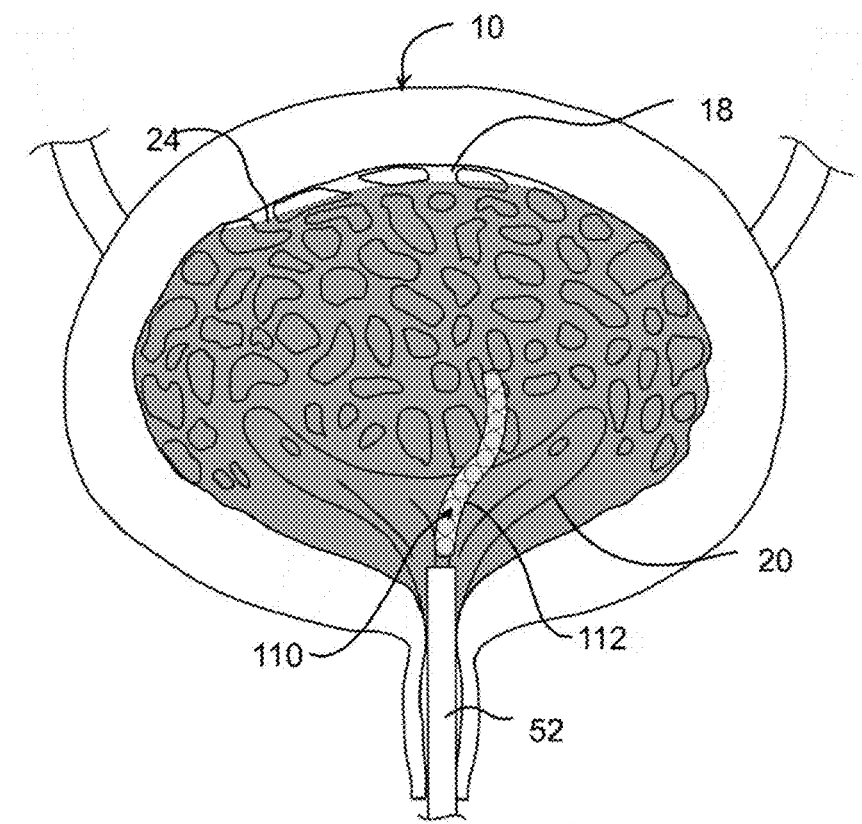

FIG. 2A illustrates delivery of particles 110 directly into the bladder 10. As shown, the bladder 10 typically contains a fluid 24 where a buoyancy of the particles 110 cause flotation towards a top of the fluid 24/cavity 18. In some variations, the fluid 24 in the bladder is urine. In alternate a fluid 24 is delivered into the bladder 10 to permit the particles 110 to float away from the trigone 20. FIG. 2A illustrates particles 110 delivered into the cavity 18 but restrained in a capsule/coating 112 wherein the particles 110 still float towards the top of the fluid 24 and away from the trigone region 20. Alternate variations can include delivery of particles into a bladder with little or no fluid where the particles will temporarily reside on the trigone region 20 until the bladder naturally fills with urine.

Figure 3A:
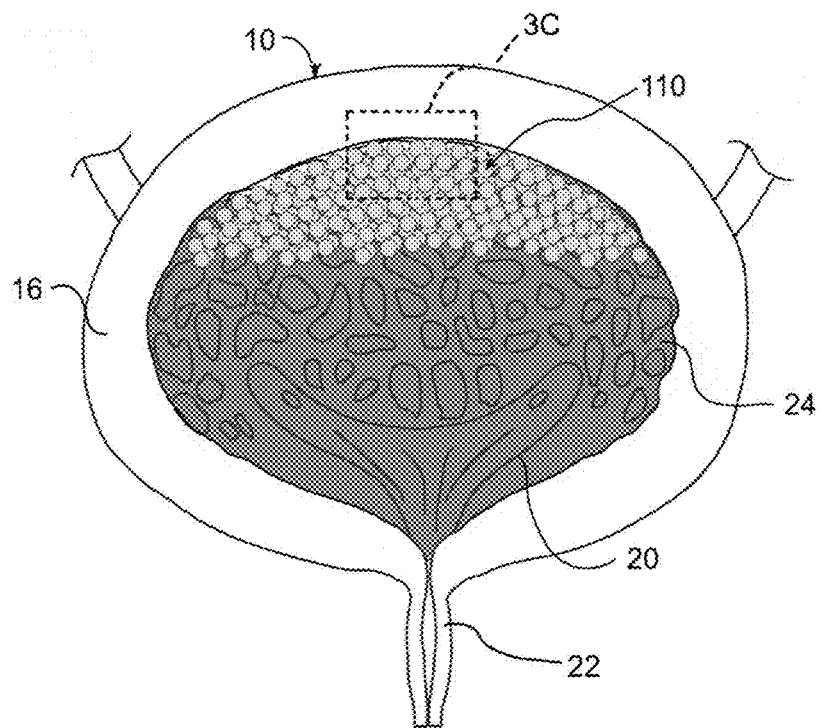
FIG. 3A shows a post deployment condition of a bladder having a number of particles deployed therein to form a temporary implant within the bladder.

FIG. 3A shows a post deployment condition of a bladder 10 having a number of particles 110 deployed therein to form a temporary implant within the bladder. As discussed below, the particles 110 can comprise micro-spheres or have any number of other shapes. As shown and discussed in additional detail below, the particles 110 accomplish several objectives. For example, a buoyancy of the particles prevents the particles from blocking the urethra 22 to allow urine to drain from the bladder. In addition, the majority of the temporary implant 110 remains separated from the trigone region 20. As discussed herein, the particles have a therapeutic or active substance that assists in preventing infection within the bladder 10 and/or urethra 22 by preventing or disrupting the growth of bacteria therein.

Another benefit to using a number of particles 110 is that ordinary movement of each particle 110 within the bladder 100 can cause turbulence in the urine or simple mechanical force against the bladder surface, which are additional means to prevent formation of biofilms that foster the growth of bacteria. In one variation, movement of the particles 110 during or after delivery performs a bacterial agitation within the bladder 10 or along a lining of the bladder. This bacterial agitation disrupts adherent bacteria and disrupts biofilms by mechanical action. By disrupting formation of biofilms in the bladder, the present devices 110 can reduce or eliminate bacteria growth and prevent and/or treat UTIs by preventing/maintain bacteria at levels that are unable to cause a UTI by mechanical action in addition to any therapeutic effect.

Figure 3B:
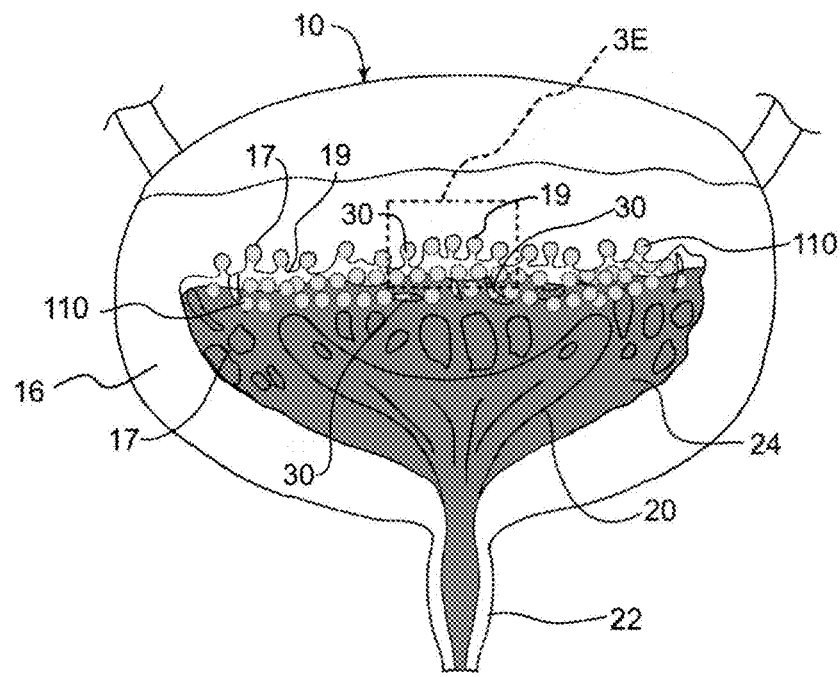
FIG. 3B illustrates a mechanism by which a sufficient number of particles are retained for a significant period of time even though the bladder goes through a series of cycles in of filling and clearing of urine.

FIG. 3B illustrates a mechanism by which a sufficient number of particles 110 are retained for a significant period of time even though the bladder goes through a series of cycles in of filling and clearing of urine. As discussed above, contraction of the bladder (from a distended state shown in FIG. 3A) occurs through contraction of muscles in the walls 16 of the bladder 10. As the muscles contract, the rugae 17, forming ridges in the lining of the bladder 10, fold such that the walls of the rugae 19 close together. Since the particles 110 are designed to have a pre-determined size range and because the particles 110 are buoyant in urine 24, the particles 110 are forced against the walls 19 of the rugae 17 as they fold. This effect causes retention of particles 110 within the folds of the rugae 17. Because the level of urine 24 declines, the remaining particles 110 at the surface or top of the urine essentially coat the surface of the bladder 10 as it contracts. The bladder 110 naturally contracts at the top and then towards the mid-section, thereby enabling a significant portion of particles 110 to be retained at the interface between the surface of the urine 24 and the surface wall of the bladder.

Figure 3C:
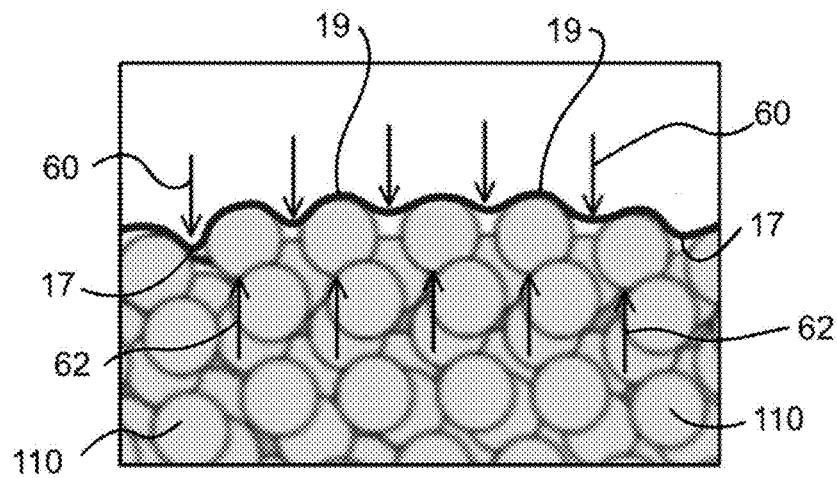
FIGS. 3C to 3E provides illustrations to demonstrate the ability of the bladder to improve retention of the particles.
Figure 3D:
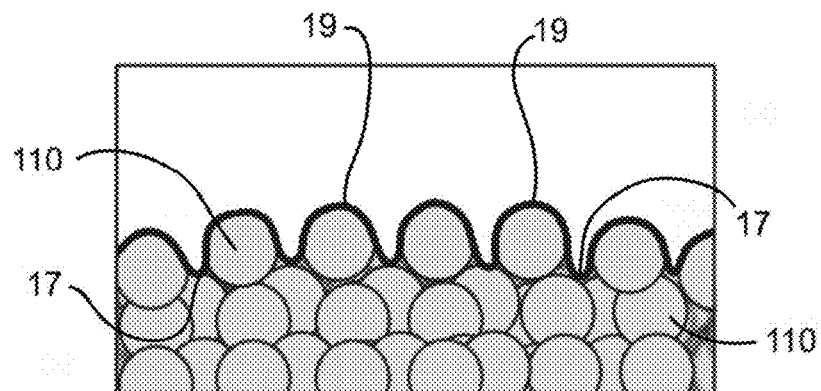
Figure 3E:
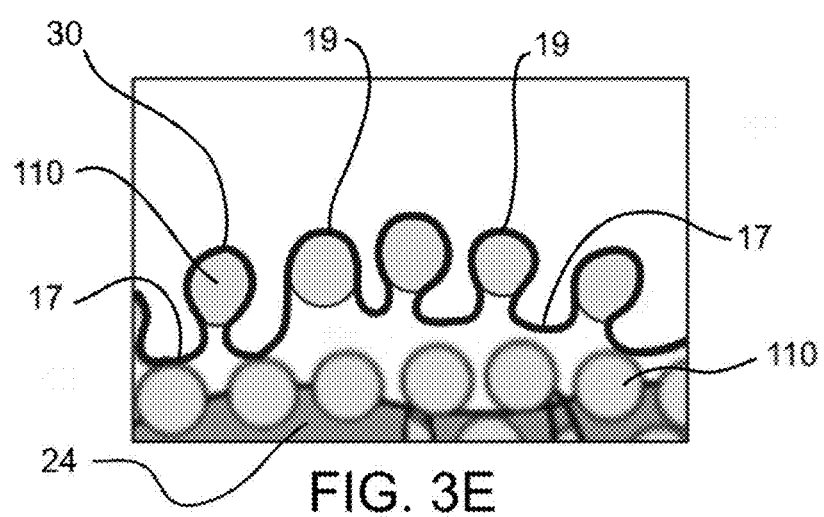

FIGS. 3C and 3E are magnified illustrations of similarly marked areas of FIGS. 3A and 3B. FIG. 3C is intended to illustrate that as the bladder contracts, the walls 19 of the rugae 17 apply a force 60 to the topmost particles 110, while the urine causes a buoyant force 62 on the particles 110 causing particles 110 that are adjacent to the rugae 17 and rugae walls 19 to be held against the lining of the bladder. FIG. 3D illustrates further folding of the rugae walls 19 causing the particles 110 to be trapped within the rugae 17 folds. Clearly, FIG. 3D is intended for illustrative purposes only and the illustrated size ratio between particles 110 and rugae 17 are intended to illustrate the mechanism of action by which particles are retained over an increased duration of time and over cycles of bladder emptying and filling. FIG. 3E illustrates further contraction of the bladder as the receding level of urine 24 draws particles 110 away from particles 110 retained in folds of rugae 30.

While the invention described herein can employ any range of particle size, in one example, it was found that human rugae have a cleft width of between 200-400 micrometers. Therefore, experiments have shown that sizes less than 400 micrometers show best retention. It is believed that commercially optimum retention size is around 100 micrometers However, the size of the particles will depend on the bladder size of the individual (or animal) being treated. Infants and children will likely have a different optimal particle size compared to adults.

The size and buoyancy of the particles allow benefits specific to the bladder. For example, in certain variations of the methods and devices, the size of the particles allows for passage through the urethra, when needed, to prevent blockage. The buoyancy and relatively small size of the particles aid in retention of the particles in the bladder regardless of any forces acting on the particle by the bladder walls during voiding of the bladder. Particles that are too large can be expelled by such forces during voiding. The retention of the particles also benefits patients since the particles fill any post-void residual space of the contracted bladder, which displaces any urine that would otherwise remain within the bladder and possibly cause a UTI. If the contracted bladder contains excess particles, the size of the particles allows for passing through the urethra to avoid any increase in the frequency of urination.

Figure 4A:
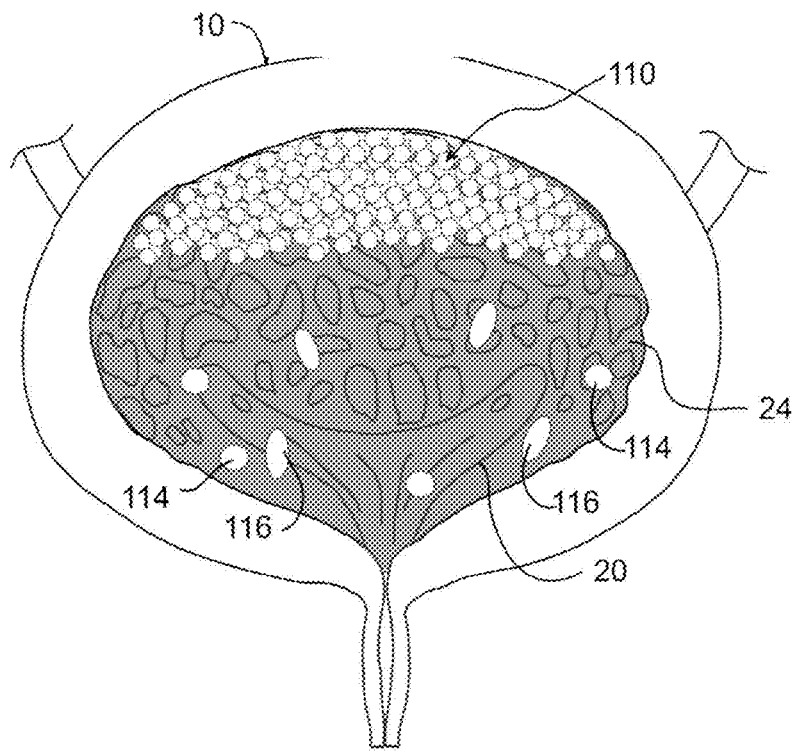
FIGS. 4A and 4B shows the use of additional secondary particles.
Figure 4B:
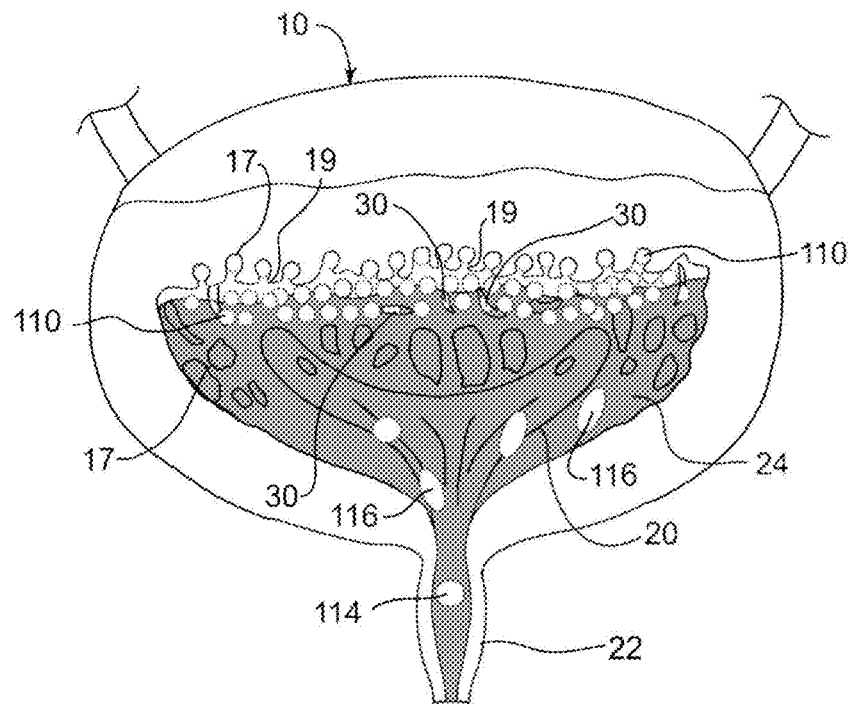

FIGS. 4A and 4B illustrate additional variations of retention of particles 110, 114, 116 within the bladder 10, where particles 114 and 116 represent secondary particles that are configured with different fluid and/or structural properties than particles 110 while still having the same or additional therapeutic properties. As shown, particles 114, 116 can be designed with different shapes or sizes that do not allow for retention by the wall of the bladder. Alternatively, or in addition, such second particles can be designed to sink within urine 24. In some variations, the secondary particles 114 and 116 can be added using a volume that does not cause irritation at the trigone region 20. As shown in FIG. 4B, as the bladder 10 contracts and particles 10 are retained within the rugae 30, the secondary particles can discharge through the urethra 22. The use of secondary particles can also assist in delivery the therapeutic effect to regions of the bladder that retain urine after contraction. Such a region is called a cystocele, also known as a prolapsed, herniated, dropped or fallen bladder. In such a condition, the ligaments that hold the bladder and surrounding muscles stretch or weaken, allowing the bladder to sag. Therefore, the sagging region will can be treated by the non-floating particles 114, 116.

Figure 5A:
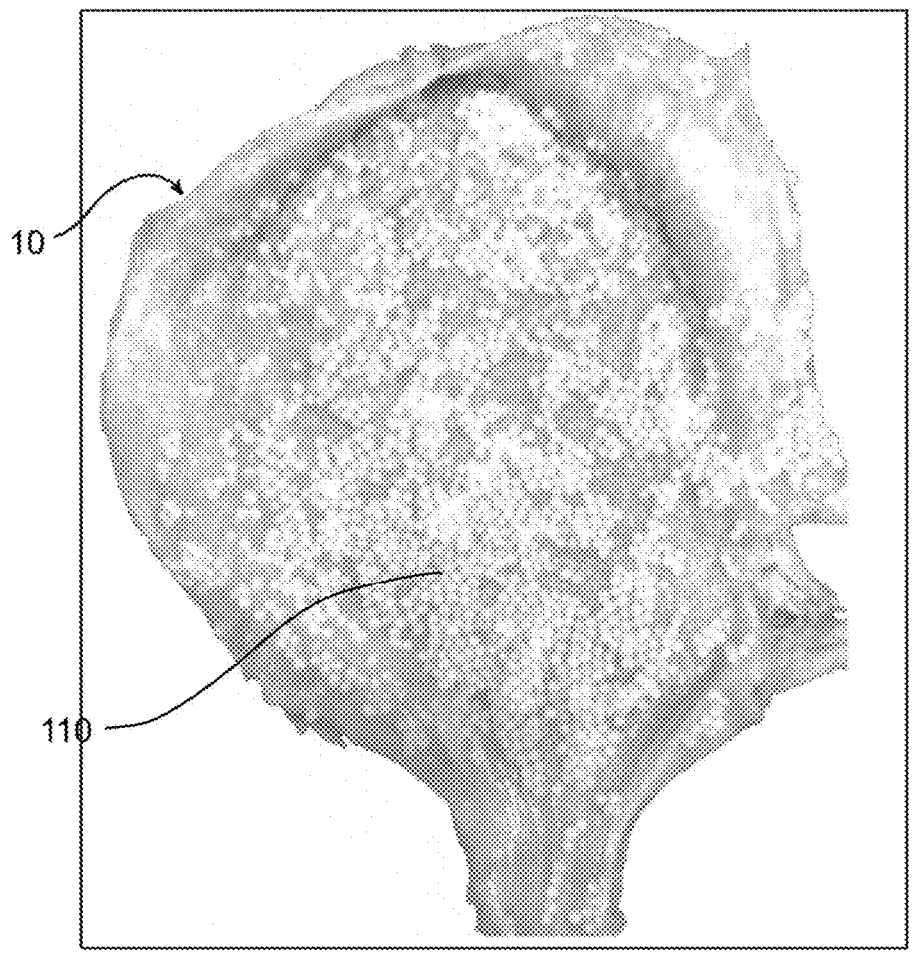
FIG. 5A shows a photograph of an excised pig bladder that retained particles in the manner discussed herein.
Figure 5B:
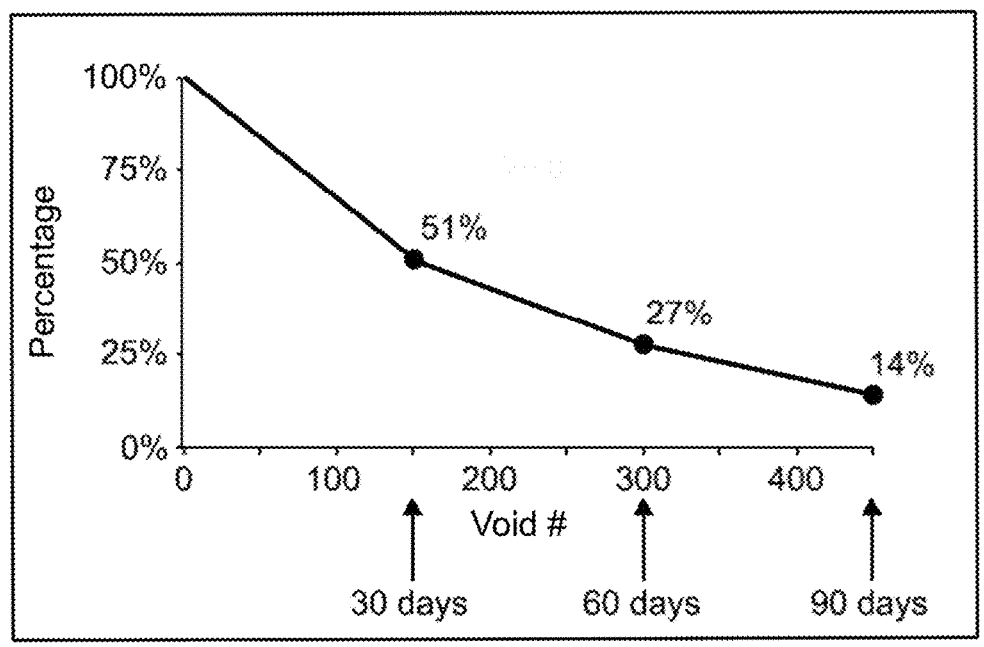
FIG. 5B shows a graph of projected retention of particles over 90 days.

FIG. 5A is a photograph of an excised pig bladder 10 in which particles 110 were deployed in the manner described herein. As shown, particles 110 coated a surface of the bladder. FIG. 5B illustrates data from excised pig bladders showing a graph of the projected percentage of retention of particles at 30, 60, and 90 days.

Figure 6A:
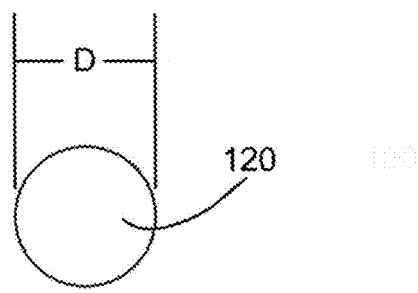
FIG. 6A to 6D show variations of shapes of particles for use as described herein.
Figure 6B:
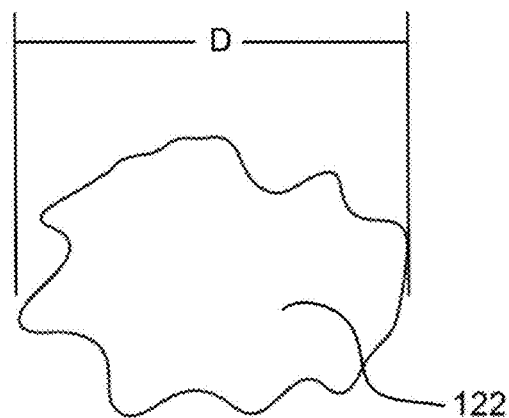
Figure 6C:
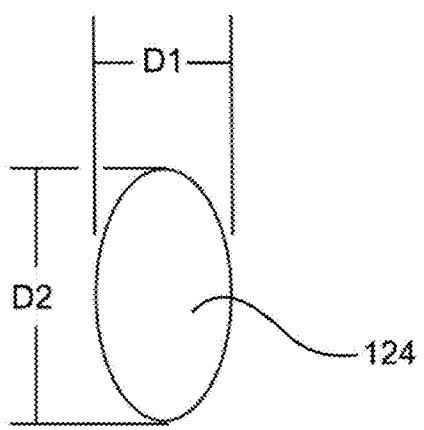
Figure 6D:
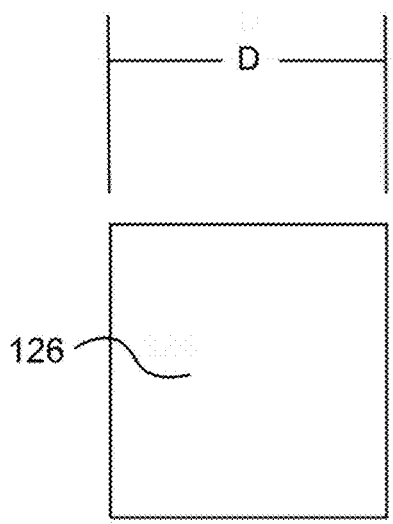

FIGS. 6A to 6D illustrate various shapes of particles 120, 122, 124, 126 that can be used either alone or in combination for treatment as described above. FIG. 6A illustrates a typical particle or microsphere 120 shape having diameter D that can be used. In contrast, FIG. 6B shows an irregular shape 122 where a diameter D can be taken along the largest or smallest dimension. FIG. 6C illustrates non-symmetrical shapes 124 having a first diameter D1 and second diameter D2. FIG. 6D illustrates a cube shape 126. As noted herein, any combination of shapes can be used to effect the therapeutic treatment and retention of the therapy device.

The variations of the implants described herein can contain any number of active agents that ultimately reduce bacterial formation or re-adherence within the organ. In one example, the particles comprise silver sulfadiazine embedded within polylactic-co-glycolic acid or silver sulfadiazine coated glass microspheres. However, any therapeutic substance can be used as an active agent.

The active agents can comprise coatings and/or can be embedded within a matrix of the carrier material that forms the particle-particle-implant whereby the matrix releases the agent (e.g., granules). Some examples of such agents include the following (as well as combinations of various agents). In one variation, the active agent can comprise one or more substances that control pH of the urine to prevent crystallization of solute onto the device body; substances that prevent bacterial enzyme urease from activity; urease inhibitor e.g., N-(n-butyl) thiophosphoric triamide (NBPT). The agent can also decrease effective solutes for crystallization within the urine. For example, the matrix or device body can be coated with chelating agents, e.g., ethylenediaminetetraacetic acid (EDTA), dimercaptosuccinic acid, dimercaprol, penicillamine. The agent can decrease bacterial activity to prevent encrustation of the carrier material or device body. For example, the carrier material can be coated with antibacterial agents, a compound containing silver e.g., (silver nitrate, elemental silver, etc.), another substance such as an antibiotic drug, copper, zinc, gold, antibacterial nanoparticles, liposomes, aptamers, dendrimers, antimicrobial peptides, inorganic or polymeric nanoparticles, smart nanoparticles. etc. The active agent can comprise a coating that prevents the formation of a biofilm. A biofilm typically comprises any syntrophic consortium of microorganisms in which cells stick to each other or to a surface. These cells become embedded within an extracellular matrix that is composed of extracellular polymeric substances. Because the matrix has a three-dimensional structure it provides a means for microbes and other bacteria to grow and multiply. By disrupting formation of biofilms in the bladder, the present devices 100 can reduce or eliminate bacteria growth within the bladder. Alternatively, the particle-implants can maintain the bacteria at levels that are unable to cause a UTI.

In those variations of particle-implants that require degradation, fracturing of the particle-implant can occur through mechanical compression (i.e. cycling of bladder emptying), fracturing of device through other mechanical action (e.g., snare, suction, scissors, etc), hydrolytic degradation in aqueous environment, introduction of enzymatic or chemical agent into bladder, environment (e.g., bladder irrigation with hydrogen peroxide or naturally over time), systemic administration of agent which changes composition of urine to trigger degradation (e.g., methenamine hippurate to acidify urine). Moreover, the carrier materials used herein can be configured such that if they become stuck in the urethra or neck of the bladder, the increased flow or turbulence of the urine attempting to flow through a restricted area will cause increased or turbulent flow. In such cases, the carrier material can be selected such that it breaks down or erodes when subject to increased flow or turbulence.

For example, such coatings include enzymes that degrade the biofilm extracellular matrix, such as dispersin B and deoxyribonuclease, nitric oxide, etc. The agent can include materials and/or coatings that decrease the affinity of crystals from attaching to the device (e.g., polyurethane, PTFE)

As for other details of the present invention, materials and manufacturing techniques may be employed as within the level of those with skill in the relevant art. The same may hold true with respect to method-based aspects of the invention in terms of additional acts that are commonly or logically employed. In addition, though the invention has been described in reference to several examples, optionally incorporating various features, the invention is not to be limited to that which is described or indicated as contemplated with respect to each variation of the invention.

Various changes may be made to the invention described. For example, the invention includes combinations of aspects of the variations of the devices described herein as well as the combination of the variations themselves. Also, any optional feature of the inventive variations may be set forth and claimed independently, or in combination with any one or more of the features described herein. Accordingly, the invention contemplates combinations of various aspects of the embodiments or combinations of the embodiments themselves, where possible. Reference to a singular item, includes the possibility that there are plural of the same items present. More specifically, as used herein and in the appended claims, the singular forms "a," "and," "said," and "the" include plural references unless the context clearly dictates otherwise.

It is important to note that where possible, aspects of the various described embodiments, or the embodiments themselves can be combined. Where such combinations are intended to be within the scope of this disclosure.

We claim:

1. A method for improving retention in a urinary bladder, the method comprising:
    providing a plurality of particles each having therapeutic properties where at least each particle of the plurality of particles has a buoyancy resulting in flotation of the plurality of particles in a urine contained in the urinary bladder, where a size of each particle of the plurality of particles falls within a pre-determined size range; and
    delivering the plurality of particles through a urethra into the urinary bladder wherein the plurality of particles float to a surface of the urine, such that upon contraction of the urinary bladder one or more rugae on a wall of the urinary bladder contracts to form a fold in tissue, where a combination of the buoyancy and the pre-determined size range of the plurality of particles causes the one or more rugae to encase the plurality of particles in the fold of tissue such that a number of particles is retained in the urinary bladder over a series of cycles in which the urinary bladder refills and empties with urine.

2. The method of claim 1, wherein each particle of the plurality of particles includes a therapeutic substance.

3. The method of claim 2, where the therapeutic substance is selected from a group consisting of a urease inhibitor, a chelating agent, an antibacterial agent, an enzyme, and a combination thereof.

4. The method of claim 2, wherein each particle of the plurality of particles further includes a carrier substance.

5. The method of claim 4, wherein the carrier substance comprises a degradable material.

6. The method of claim 4, wherein the therapeutic substance is located within the carrier substance.

7. The method of claim 4, wherein the therapeutic substance coats the carrier substance.

8. The method of claim 4, wherein the carrier substance comprises a polymer.

9. The method of claim 4, wherein the carrier substance comprises a glass material.

10. The method of claim 4, wherein the carrier substance is porous.

11. The method of claim 1, further comprising providing a plurality of secondary particles each having therapeutic properties where at least each secondary particle of the plurality of secondary particles has a buoyancy resulting in sinking of the plurality of particles in the urine contained in the urinary bladder.

12. The method of claim 1, where a density of each particle of the plurality of particles is less than 1 kg/m^3.

13. The method of claim 1, where the pre-determined size range is less than 400 micrometers.

14. The method of claim 1, where delivering the plurality of particles through the urethra into the urinary bladder causes a mechanical disruption of a biofilm within the urethra or bladder.

15. The method of claim 1, where delivering the plurality of particles through the urethra comprises delivering the plurality of particles using a syringe.

* * * * *